United States Patent [19]
Meul et al.

[11] Patent Number: 5,149,869
[45] Date of Patent: Sep. 22, 1992

[54] PROCESS FOR THE PRODUCTION OF DIMETHYLCYCLOPROPANECARBOXYLIC ACID

[75] Inventors: Thomas Meul, Visp; Ulrich Kämpfen, Brig, both of Switzerland

[73] Assignee: Lonza Ltd., Gampel/Valais, Switzerland

[21] Appl. No.: 803,066

[22] Filed: Dec. 6, 1991

[30] Foreign Application Priority Data

Dec. 17, 1990 [CH] Switzerland ................. 3991/90

[51] Int. Cl.$^5$ ............................................ C07C 61/04
[52] U.S. Cl. ................................. 562/506; 560/124
[58] Field of Search ..................... 560/124; 562/506

[56] References Cited

FOREIGN PATENT DOCUMENTS 0048301 3/1982 European Pat. Off. .
0093511 11/1983 European Pat. Off. .
2751133 5/1979 Fed. Rep. of Germany .

OTHER PUBLICATIONS

Chemical Abstracts, vol. 7, (1913), p. 3965 and of Chemisches Zentralblatt, (1913), II, pp. 2130 and 2131, both of which abstract N. Kishner, J. Russ. Phys. Chem. Soc., 45, (1913), 57ff.
Patent Abstracts of Japan, E Field, vol. 7, No. 285, Dec. 20, 1983, p. 164 C201.
Chemical Abstracts, vol. 68, No. 29, Japan 1968, p. 2058, 21563e.
E. R. Nelson et al., J. Am. Chem. Soc., 79, (1957), pp. 3467 to 3469.
S. R. Landor et al., J. Chem. Soc. (C), (1967), pp. 2495 to 2500.
Houben-Weyl, "Methoden der organischen Chemie", 4th Ed., vol.: Phosphorverbindungen I, pp. 173 to 176 (1982).

*Primary Examiner*—Michael L. Shippen
*Attorney, Agent, or Firm*—Fisher, Christen & Sabol

[57] ABSTRACT

A process for the production or R,S-2,2-dimethylcyclopropanecarboxylic acid starting from isobutylene oxide and a phosphonoacetic acid trialkyl ester. In this way, first the R,S-2,2-dimethylcyclopropanecarboxylic acid-$C_1$–$C_4$ alkyl ester is formed, which then is hydrolyzed to the corresponding acid. R,S-2,2-Dimethylcyclopropanecarboxylic acid is an important intermediate product for the production of S-(+)-2,2-dimethylcyclopropanecarboxamide.

8 Claims, No Drawings

PROCESS FOR THE PRODUCTION OF DIMETHYLCYCLOPROPANECARBOXYLIC ACID

BACKGROUND OF THE INVENTION

1. Field Of The Invention

The invention relates to a new process for the production of R,S-2,2-dimethylcyclopropanecarboxylic acid (which is sometimes abbreviated below as R,S-2,2-DMCPCS).

2. Background Art

R,S-2,2-DMCPCS is an important intermediate product for the production of S-(+)-2,2-dimethylcyclopropanecarboxamide [abbreviated sometimes below as S-(+)-2,2-DMCPCA], in which R,S-2,2-DMCPCS is converted by resolution of racemates to the optically pure S-(+)-enantiomer and is subsequently converted via acid chloride to S-(+)-2,2-DMCPCA (see European Published Patent Appln. No. 093511). S-(+)-2,2-DMCPCA is used in turn as initial material for the production of the dehydropeptidase inhibitor cilastatin, which in treatment is administered together with penem or carbapenem antibiotics to prevent the deactivation of the antibiotics by a renal dehydropeptidase in the kidney (see European Published Patent Appln. No. 048301).

From the literature, several processes for the production of R,S-2,2-DMCPCS are known.

N. Kishner. J. Russ. Phys. Chem. Soc., 45, (1913), page 957 ff, describes a three-stage synthesis for the production of R,S-2,2-DMCPCS starting from phorone. In this process, the phorone is converted to a pyrazoline derivative in the first stage with hydrazine. The pyrazoline derivative is converted to a 2,2-dimethylcyclopropane derivative in the second stage with potassium hydroxide, in the presence of platinum. The 2,2-dimethylcyclopropane derivative is then oxidized to R,S-2,2-DMCPCS in the third stage with potassium permanganate. The drawback of this process is that the production of the intermediate pyrazoline has to be performed with the highly toxic and carcinogenic hydrazine.

E. R. Nelson et al., J. Am. Chem. Soc., 79, (1957), pages 3467 to 3469, also describes a three-stage process for the production of R,S-2,2-DMCPCS starting from 2,2-dimethylpropane-1,3-diol. In this way, the 2,2-dimethylpropane-1,3-diol is first converted with p-toluenesulfonyl chloride to the ditosylate derivative, the latter is then reacted in the second stage with potassium cyanide to the 2,2-dimethylcyclopropanenitrile, which then is hydrolyzed in the third stage to the corresponding acid. A great drawback of this process is that, in this way, large amounts of potassium tosylate accumulate for disposal as waste product and moderate yields (28 percent) are attained.

S. R. Landor et al., J. Chem. Soc. (C), (1967), page 2492 to 2500, describes a process for the production of R,S-2,2-DMCPCS starting from 2-methylbutenoic acid ethyl ester, which first is converted to the 2,2-dimethylcyclopropanecarboxylic acid ester with a sulfurylide derivative, which then is hydrolyzed to the corresponding acid. A great drawback of this process lies in the fact that the 2,2-dimethylcyclopropanecarboxylic acid ester is obtained in very poor yield (9 percent) and, thus, the total yield of the corresponding acid is still smaller. Another drawback of this process consists in the use of the expensive sulfurylide derivative.

Another process for the production of R,S-2,2-DMCPCS is described in West German Patent No. 2,751,133. In this process, first 4-chloro-4,4-dimethylbutyric acid ester is produced from a lactone derivative and the latter is cyclized in the presence of alcoholates to R,S-2,2-dimethylcyclopropanoic acid ester, which is subsequently hydrolyzed. A great drawback of this process lies in the fact that the lactone is not commercially available and has to be produced in a multistage synthesis.

BROAD DESCRIPTION OF THE INVENTION

The main object of the invention is to eliminate these drawbacks and to make available a simple and economical process for the production of R,S-2,2-dimethylcyclopropanecarboxylic acid and where the R,S-2,2-DMCPCS is obtained with good yields. Other objects and advantages of the invention are set out herein or are obvious herefrom to one skilled in the art.

The objects and advantages of the invention are achieved by the invention process.

According to the invention, the process for the production of R,S-2,2-DMCPCS is performed so that isobutylene oxide of the formula:

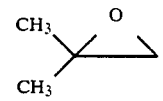

is converted with a phosphonoacetic acid trialkyl ester of the formula:

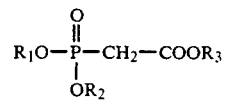

wherein $R_1$, $R_2$ and $R_3$ are the same or different and are a $C_1$–$C_4$ alkyl group, branched or unbranched, in the presence of a base in an R,S-2,2-dimethylcyclopropanecarboxylic acid-$C_1$–$C_4$ alkyl ester of the formula:

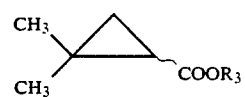

wherein $R_3$ has the above meaning, and the ester is hydrolyzed to the end product in the presence of a base.

DETAILED DESCRIPTION OF THE INVENTION

The phosphonoacetic acid trialkyl ester can be obtained by reaction of a trialkoxyphosphine with a haloacetic acid ester [Houben-Weyl, Methoden der organischen Chemie (Methods of Organic Chemistry), 4th edition, Vol.: Phosphorverbindungen I (Phosphorus Compounds I), pages 173 to 176]. Suitably, phosphonoacetic acid triethyl ester or diethylphosphonoacetic acid isopropyl ester is used as the phosphonoacetic acid trialkyl ester. Preferably phosphonoacetic acid triethyl ester is used.

Suitably, the reaction of the phosphonoacetic acid trialkyl ester takes place with stoichiometric amounts of isobutylene oxides. The reaction of the phosphonoacetic acid trialkyl ester with isobutylene oxide is performed in the presence of a base. As the base, for example, an alkali hydride, such as, sodium hydride, potassium hydride or lithium hydride, can be used. Suitably, the base is used equimolar to the phosphonoacetic acid trialkyl ester. The reaction temperature is suitably between 100° and 140° C., preferably between 110° and 130° C. As the solvent, the high-boiling, aromatic hydrocarbons or polar solvents are used. For example, xylene or xylene-isomer mixtures can be used as the high-boiling, aromatic hydrocarbons. As the polar solvent, for example, glycol ethers, such as, diethylene glycol dimethyl ether, can be used. Preferably, a high-boiling, aromatic hydrocarbon, such as, o-xylene, is used as the solvent.

The R,S-2,2-dimethylcyclopropanecarboxylic acid-$C_1$-$C_4$ alkyl ester is then suitably hydrolyzed to the desired R,S-2,2-DMCPCS, without isolation, in the presence of a base. Suitably, an alkali hydroxide is used as the base for the ester hydrolysis. As the alkali hydroxide, for example, sodium hydroxide or potassium hydroxide, can be used. The ester hydrolysis is suitably performed with 1 to 2 moles of base, preferably with 1.2 to 1.5 moles, relative to 1 mol of R,S-2,2-dimethylcyclopropanecarboxylic acid ester. Suitably, the ester hydrolysis takes place at a temperature of 40° C. up to reflux temperature, preferably at reflux temperature. The ester hydrolysis is suitably performed in a mixture of one of said high-boiling, aromatic hydrocarbons with an aqueous alcoholic solution. As the alcohols, lower alcohols, such as, methanol or ethanol, can be used.

The R,S-2,2-dimethylcyclopropanecarboxylic acid can be isolated after 2 to 3 hours of reaction time, for example, by acidifying the reaction mixture and subsequent extraction.

EXAMPLE

Production of R,S-2,2-Dimethylcyclopropanecarboxylic acid 4.8 g (0.16 mol) of sodium hydride (80 percent in white oil) in 20.0 ml of o-xylene was introduced in a 150 ml three-necked flask and mixed within 30 minutes with a solution of 36.1 g (0.16 mol) or phosphonoacetic acid triethyl ester in 35.0 ml of o-xylene by instillation at room temperature. As soon as the H₂ development was completed, 10.8 g (0.15 mol) of isobutylene oxide (BASF AG) in 20.0 ml of o-xylene was added. Then, the reaction mixture was heated for 2 hours to 120° C., cooled to room temperature and mixed with 50.0 ml of water. The lower aqueous phase was separated. The xylene phase was mixed with a solution of 8.0 g of NaOH in 30.0 ml of water and 50.0 ml of ethanol and refluxed for 2 hours. Then, the organic phase was separated. The aqueous phase was adjusted to pH 1 with concentrated HCl and extracted twice with 50.0 ml of n-hexane each. The hexane phases were combined, dried and concentrated by evaporation. The residue was distilled in a water jet vacuum. 8.8 g of colorless R,S-2,2-dimethylcyclopropanecarboxylic acid solution with a content of 98 percent of R,S-2,2-dimethylcyclopropanecarboxylic acid and a boiling point of 90° C. (2.5 mbars) was obtained, which corresponded to a yield of 50 percent, relative to the isobutylene oxide used.

What is claimed is:

1. Process for the production of R,S-2,2-dimethylcyclopropanecarboxylic acid of the formula:

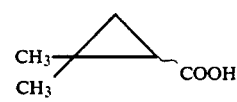

comprising converting isobutylene oxide of the formula:

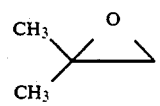

with a phosphonoacetic acid trialkyl ester of the formula:

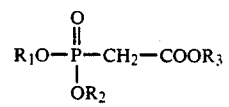

wherein $R_1$, $R_2$ and $R_3$ are the same or different and are a $C_1$-$C_4$ alkyl group, branched or unbranched, in the presence of a base in an R,S-2,2-dimethylcyclopropanecarboxylic acid-$C_1$-$C_4$ alkyl ester of the formula:

wherein $R_3$ has the above meaning, and hydrolyzing the ester to the end product in the presence of a base.

2. Process according to claim 1 wherein phosphonoacetic acid triethyl ester is used as the phosphonoacetic acid trialkyl ester.

3. Process according to claim 2 wherein the phosphonoacetic acid trialkyl ester is reacted in the presence of an alkali hydride as a base at a temperature of 100° to 140° C.

4. Process according to claim 1 wherein the ester hydrolysis is performed in the presence of an alkali hydroxide as a base at a temperature of 40° C. up to reflux temperature.

5. Process according to one of claim 4 wherein the process is performed without isolation of the intermediate stage.

6. Process according to claim 1 wherein the phosphonoacetic acid trialkyl ester is reacted in the presence of an alkali hydride as a base at a temperature of 100° to 140° C.

7. Process according to one of claim 1 wherein the process is performed without isolation of the intermediate stage.

8. Process according to one of claim 2 wherein the process is performed without isolation of the intermediate stage.

* * * * *